(12) United States Patent  
Fish et al.

(10) Patent No.: US 11,544,235 B2
(45) Date of Patent: Jan. 3, 2023

(54) SMART STORAGE CONTAINER APPARATUS, SYSTEM AND METHOD THEREOF

(71) Applicant: 19LABS INC., Menlo Park, CA (US)

(72) Inventors: Ram Adva Fish, Menlo Park, CA (US); Gerald Charles Horel, British Columbia (CA)

(73) Assignee: 19LABS INC., Menlo Park, CA (US)

( * ) Notice: Subject to any disclaimer, the term of this patent is extended or adjusted under 35 U.S.C. 154(b) by 0 days.

(21) Appl. No.: 15/480,418

(22) Filed: Apr. 6, 2017

(65) Prior Publication Data

US 2017/0293739 A1 Oct. 12, 2017

Related U.S. Application Data

(60) Provisional application No. 62/320,207, filed on Apr. 8, 2016.

(51) Int. Cl.
| | |
|---|---|
| *G06F 16/21* | (2019.01) |
| *G06F 16/23* | (2019.01) |
| *G06F 16/903* | (2019.01) |
| *G16H 40/20* | (2018.01) |

(52) U.S. Cl.
CPC .......... *G06F 16/21* (2019.01); *G06F 16/2379* (2019.01); *G06F 16/90344* (2019.01); *G16H 40/20* (2018.01)

(58) Field of Classification Search
CPC .. G06F 19/3456; G06F 16/21; G06F 16/2379; G06F 16/90344; G16H 20/10
USPC ........................................................ 715/746
See application file for complete search history.

(56) References Cited

U.S. PATENT DOCUMENTS

| 7,477,758 B2* | 1/2009 | Piirainen | G01S 15/523 701/44 |
|---|---|---|---|
| 2009/0235150 A1* | 9/2009 | Berry | G06F 16/48 707/E17.014 |
| 2010/0134243 A1* | 6/2010 | Colley, III | G07C 9/00896 340/5.7 |
| 2011/0130636 A1 | 6/2011 | Daniel et al. | |
| 2012/0011253 A1 | 1/2012 | Friedman et al. | |
| 2014/0297487 A1* | 10/2014 | Bashkin | A47B 96/02 705/28 |

(Continued)

FOREIGN PATENT DOCUMENTS

WO WO-2016023081 A1 * 2/2016 ............... B25H 3/02

*Primary Examiner* — Stephen S Hong
*Assistant Examiner* — Broderick C Anderson
(74) *Attorney, Agent, or Firm* — Inventive Law Inc.; Jim H. Salter

(57) ABSTRACT

A smart storage container apparatus and method, the apparatus comprising at least one storage compartment and a display, and is configured to download basic local configuration information corresponding to the apparatus, locally adjust the downloaded information according to local conditions of content of the at least one storage compartment, and based on the adjusted configuration information, adapt a local configuration database. Additionally, a method comprising downloading basic local configuration information corresponding to a smart storage apparatus comprising, locally adjusting the downloaded information according to local conditions of content of the at least one storage compartment, and based on the adjusted configuration information, adapting a local configuration database.

20 Claims, 4 Drawing Sheets

(56) References Cited

U.S. PATENT DOCUMENTS

2014/0330103 A1 11/2014 Yoo
2017/0340221 A1* 11/2017 Cronin ................... A61B 5/747
2018/0102011 A1* 4/2018 Phillips ................. G06F 3/0486

* cited by examiner

SMART STORAGE CONTAINER APPARATUS, SYSTEM AND METHOD THEREOF

FIELD OF THE INVENTION

The present disclosure generally relates to smart first-aid kits, and more specifically to facilitating use of such kits.

BACKGROUND

Some known first aid kits include lists of contents, some with illustrative drawings. Additionally, there are known first aid guides. However, it is usually not practical to continuously monitor which equipment is missing and/or dislocated. Additionally, identifying in emergency condition exactly which equipment can be used for the specific condition and where it is stored, may cost expensive time and risk lives.

SUMMARY

According to an aspect of some embodiments of the present invention there is provided a smart storage container apparatus including: at least one storage compartment; a display, and a processor configured to execute code instructions for: downloading basic local configuration information corresponding to the apparatus; locally adjusting the downloaded information according to local conditions of content of the at least one storage compartment; and based on the adjusted configuration information, adapting a local configuration database.

Optionally, the processor is configured to execute code instructions for adjusting the downloaded information according to particular features and/or to particular environment of the apparatus.

Optionally, the processor is configured to execute code instructions for adjusting the downloaded information according to at least one of a list consisting of: particular equipment, devices and/or kinds of devices stored in the apparatus, a particular structure and/or arrangement of the at least one compartments, information relevant to where the apparatus is placed.

Optionally, the processor is configured to execute code instructions for finding local discrepancies of the downloaded information from local conditions, wherein the locally adjusting is according to the local discrepancies.

Optionally, the processor is configured to execute code instructions for finding a local discrepancies of a list consisting of a missing equipment, a missing device, a missing medicine, a changed arrangement, a changed contents and a changed structure.

Optionally, wherein the processor is configured to execute code instructions for adapting a local configuration database according to a current state of the apparatus.

Optionally, the processor is configured to execute code instructions for: loading a displayable information page; scanning the displayable page for at least one keyword included in the local configuration database; augmenting the page with an enhancement corresponding to the at least one keyword; and displaying the augmented page.

Optionally, the processor is configured to execute code instructions for augmenting the page by adding to the page information about a location of an equipment item.

Optionally, the processor is configured to execute code instructions for augmenting the page by adding or changing an interactive graphic element for initiating an action, the action corresponding to an indication in the local configuration database that the action is feasible by the apparatus.

Optionally, the processor is configured to execute code instructions for augmenting the page by initiating or changing an action in response to the at least one keyword, the action corresponding to an indication in the local configuration database that the action is feasible by the apparatus.

According to another aspect of some embodiments of the present invention there is provided a smart storage method including: downloading basic local configuration information corresponding to a smart storage apparatus comprising at least one storage compartment and a display; locally adjusting the downloaded information according to local conditions of content of the at least one storage compartment; and based on the adjusted configuration information, adapting a local configuration database.

According to another aspect of some embodiments of the present invention there is provided a smart storage method including: loading a displayable information page; scanning the displayable page for at least one keyword included in the local configuration database; augmenting the page with an enhancement corresponding to the at least one keyword; and displaying the augmented page.

BRIEF DESCRIPTION OF THE DRAWINGS

Some non-limiting exemplary embodiments or features of the disclosed subject matter are illustrated in the following drawings.

In the drawings.

Figure 1:
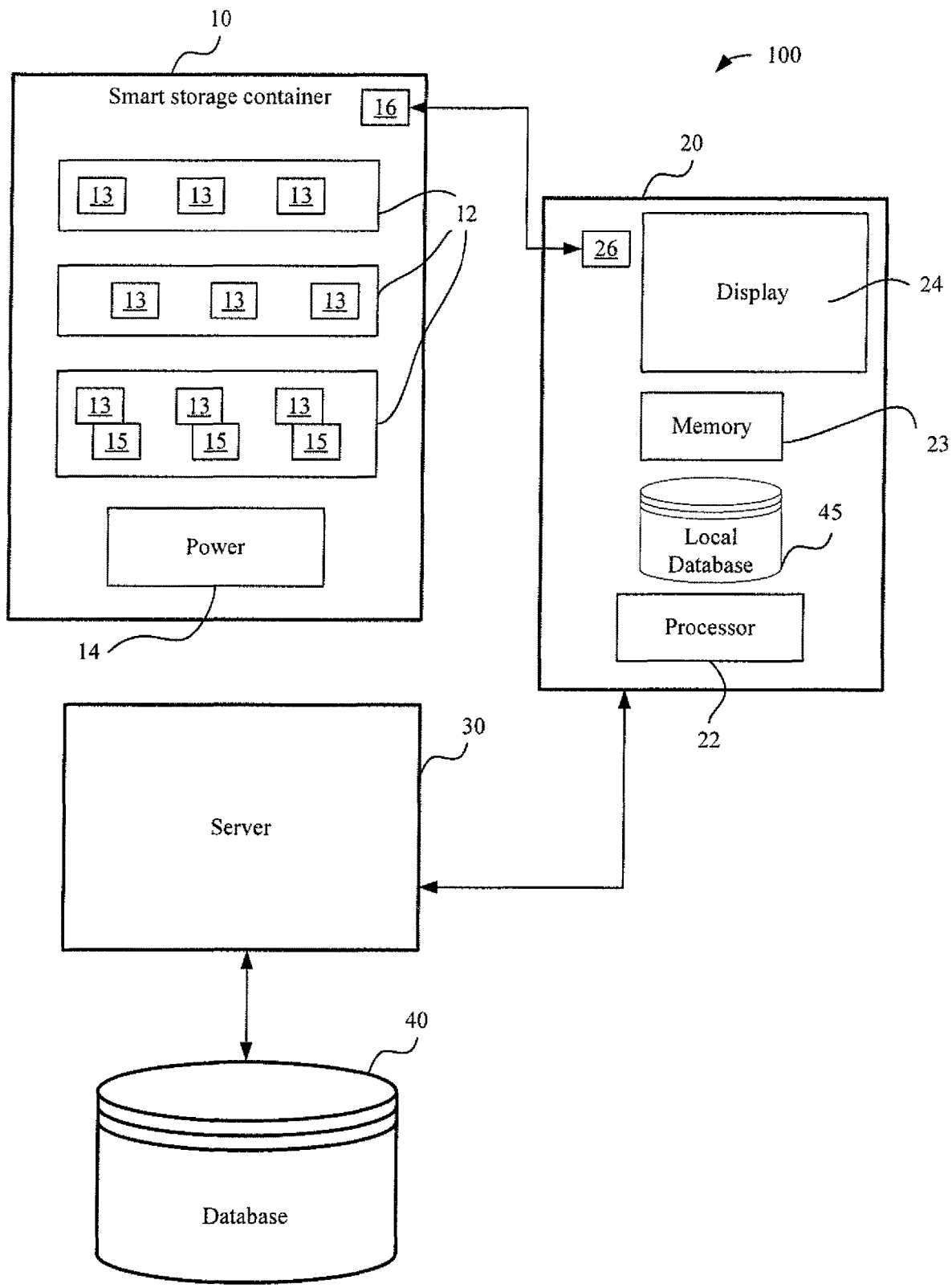
FIG. 1 is a schematic illustration of a smart storage system for controlling a smart storage container, according to some embodiments of the present invention.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true so perspective. For convenience or clarity, some elements or structures are not shown or shown only partially and/or with different perspective or from different point of views.

DETAILED DESCRIPTION

Some embodiments of the present invention provide a smart storage container apparatus, a system and a method for controlling the smart storage container. For example, the provided system and method facilitate dynamic locating of equipment of the smart container, e.g. equipment included or stored in the smart container. For example, the provided system and method facilitate performing of actions by the equipment of the smart container. In some embodiments, the smart storage container stores and/or includes equipment for first aid and/or emergency medical conditions.

In some embodiments of the present invention, the provided smart container and/or system enable continuous monitoring of which equipment is missing and/or dislocated from the container. Additionally, the provided smart container and/or system enable identifying in emergency condition exactly which equipment can be used for the specific condition and where it is stored, thus saving time and lives.

According to some embodiments of the present invention, the apparatus and/or system enable loading and displaying of database information about using the equipment of the smart container, for example a first aid and/or treatment guide. In some embodiments, the database information may be dynamically adapted to the specific smart container and its current state. By the dynamic database information, users may easily locate, learn about equipment and/or purchase equipment when indicated as missing. In some embodiments, the smart container and/or system enable chatting by text, voice and/or video with a professional, for example a nurse or a doctor.

In some embodiments of the present invention, the apparatus and/or system enhance a displayable page of the database information according to an updated configuration of the smart container apparatus. For example, the apparatus and/or system may convert keywords in texts of the displayable page and/or of a chat session to links, for example links to information about content and/or functionality of the apparatus.

Accordingly, rather than manually editing content and/or hyperlinks of displayable pages ahead of time and/or each time items are added or removed, the system automatically so adds the links to items based on a local updated database of equipment, treatable conditions and/or state of the smart container apparatus. For example, the local database may include the stored medications and supplies, sensors included in the smart container, and/or conditions treatable by equipment of the smart container apparatus. Local information about stored items and/or a current state of the smart container may be detected by detectors installed in the apparatus, for example within the container's compartments. Modifications to the local information may be performed online or offline, for example by adding keywords and relating information that enable the system to automatically enhance a displayable page a in real time, e.g. upon downloading of the page.

For example, the provided system detects within the displayable page a keyword or a keyword combination such as a name of an equipment item, and adds a link to a respective informative text element or another object informing about a respective location of the equipment item. The informing object may include, for example, a description and/or animation to regarding the item location, appearance and/or use instructions. For example, the description and/or animation may be created on the fly, e.g. upon loading of a certain page and/or contents.

In some embodiments, when the system detects that a displayable page includes keywords related to contents of the apparatus (e.g. bandages), the system automatically creates, for example, a link to a popup and/or screen that shows the user pertinent information (e.g bandage location, treatment instructions, testing instructions etc.). For example, the pertinent information includes an animation and/or a series of images, showing first in which drawer/compartment an item is located, where in the compartment the item is located, and/or image and/or description of the item.

Accordingly, the provided apparatus, system and method make use, management and/or monitoring of the actual contents and/or features of the smart container much easier.

The present invention provides a solution for use, management and/or monitoring of contents and/or features of medical treatment equipment by knowing what equipment is present in the apparatus, updating a local database with keywords respective to the equipment items, and rendering of enhanced information pages according to the local database. The enhancing may be performed when downloading a page and/or dynamically on a local device and/or on the container apparatus, for example just before displaying or in the process of displaying of the page.

The local database, in some embodiments of the present invention, includes item names related to respective locations in the smart container and/or status such as failure, missing equipment, low inventory, dysfunction and/or any other suitable indication.

Some embodiments of the present invention may include a system, a method, and/or a computer program product. The computer program product may include a tangible non-transitory computer readable storage medium (or media) having computer readable program instructions thereon for causing a processor to carry out aspects of the present invention. Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including any object oriented programming language and/or conventional procedural programming languages.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a smart storage system 100 for controlling a smart storage container 10, according to some embodiments of the present invention. In some embodiments, system 100 includes smart storage container 10, computing device 20, a server 30 and a database 40. Storage container 10 may include at least one storage compartment 12, for example a drawer, dedicated for storing one or more specific equipment, devices, and/or kinds of devices. For example, a compartment 12 may include one or more dedicated locations 13, each for a specific equipment, device or device kind. For example, a dedicated location may include a dedicated slot, sub-compartment and/or connector, suitable for storing and/or attaching a specific device or a device kind, or a specific equipment or equipment kind.

In some embodiments, dedicated location 13 includes a power charging connections, for charging a device while placed in the dedicated location. Accordingly, container 10 may include a power source 14, e.g. a battery and/or a power input port. Storage compartment 12 may include at least one detector 15 for detecting whether a corresponding equipment, device and/or device kind exists in a dedicated location 13, and/or which equipment, device and/or device kind is located in a dedicated location 13. For example, so detector 15 may include a micro-switch, a physical switch, a magnetic detector, a Hall Effect detector, an optical detector, a radio frequency identification (RFID) detector and/or any other suitable detector. Smart storage container 10 may communicate by a communication interface 16 information about arrangement and/or contents of at least one storage compartment 12. For example, communication interface 16 includes Bluetooth, cellular, Wi-Fi, Ethernet, and/or any other suitable communication interface.

Smart container 10 may communicate with and/or include computing device 20. Computing device 20 may receive from container 10 information about arrangement and/or contents of at least one storage compartment 12, for example including data detected by detectors 15. Device 20 may include at least one processor 22, a memory 23, a display 24 and a communication interface 26. For example, communication interface 26 includes Bluetooth, cellular, Wi-Fi, Ethernet, and/or any other suitable communication interface. For example, container 10 and device 20 communicate by interfaces 16 and 26. In some embodiments, device 20 may be mechanically and/or removably attached to container 10, for example, on top of container 10. In some embodiments, device 20 is integral with smart container 10. Device 20 may include a tablet computer, a smart phone device, a desktop computer, a smart display, and/or any other suitable computing device.

Server 30 may maintain database 40, for example store, update, and/or obtain data from database 40. Database 40 may include user manual and/or healthcare information such as, for example, health treatment and/or examination instructions for various conditions and/or symptoms. Local configuration of database 40 may be downloaded to device 20 via server 30, into local configuration database 45. In some embodiments, when database 40 is updated by server 30, updates to local configuration database 45 may be downloaded to device 20, automatically, by pushing the update and/or upon request from device 20, thus, for example, updating local configuration database 45. Database 40 may include displayable database pages of an interactive and/or graphical user interface (as shown, for example, in FIG. 6), which may be displayed on display 24. For example, a displayable database page may be and/or include a webpage and/or a website with multiple linked web pages. Local configuration database 45 may include local configurations of the displayable pages of an interactive and/or graphical user interface.

According to some embodiments of the present invention, computing device 20 may adapt local configuration database 45 to smart container 10, e.g. to arrangement, structure and/or contents of container 10. For example, computing device 20 may adapt the configuration of the user interface, for example automatically and/or in background of operations in device 20, to the specific smart container 10 communicating with computing device 20. For example, the adaptation may include adaptations according to capabilities and/or available content stored within smart container 10 or around smart container 10.

In some embodiments of the present invention, memory 23 includes a non-transitory storage medium storing code instructions readable and executable by processor 22, for example, causing processor 22 to carry out the methods described herein. Although the operations described herein are described as performed by device 20 and/or processor 22, in some embodiments, at least one processor 22 is in smart container 10, and/or all or some of the operations described herein are performed by smart container 10. For example, some of the operations are performed by device 20 and some by container 10.

Figure 2:
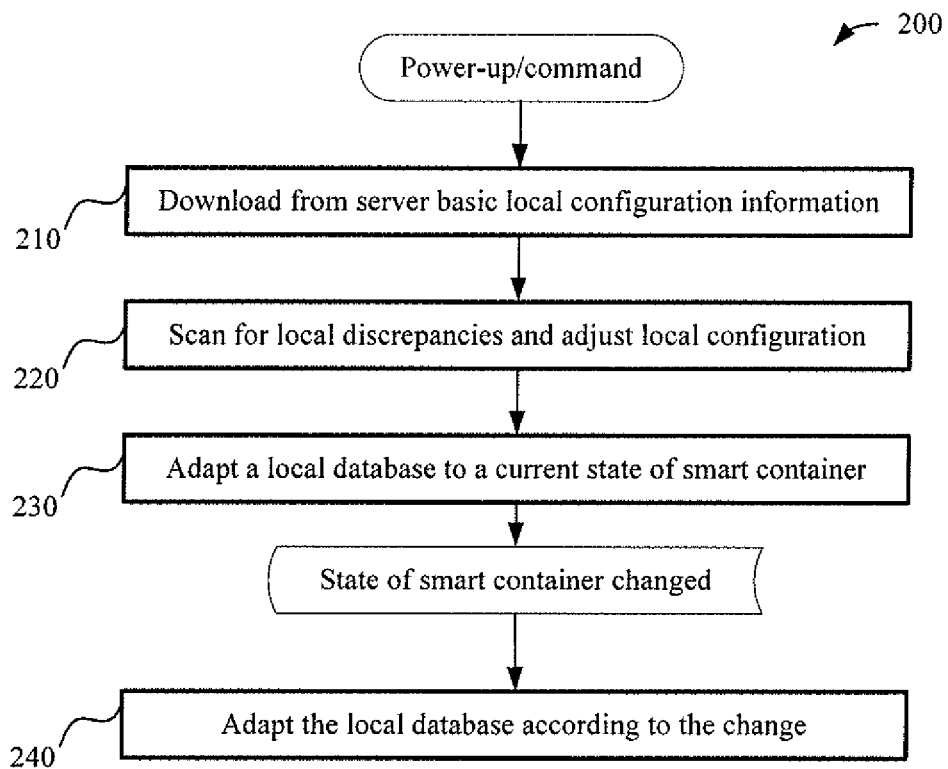
FIG. 2 is a schematic flowchart illustrating a method for adapting a local configuration database, according to some embodiments of the present invention.

Reference is now made to FIG. 2, which is a schematic flowchart illustrating a method 200 for adapting local configuration database 45, according to some embodiments of the present invention.

As indicated in block 210, processor 22 may download from server 30 basic local configuration information corresponding to a particular smart storage container 10 and/or to particular environment. For example, processor 22 may download the basic local configuration upon power up and/or restart of smart container 10 and/or device 20, and/or upon receiving of a command. For example, the basic configuration information may include instructions to configure displayable pages of database 40 according to particular equipment, devices and/or kinds of devices stored and/or storable in container 10, a particular structure and/or arrangement included in container 10, for example particular structure and/or arrangement of storage compartments 12, information relevant to where the particular container 10 is placed, and/or any other suitable local configuration.

As indicated in block 220, processor 22 may scan the downloaded basic local configuration information, find local discrepancies of the downloaded information from local conditions such as a missing equipment, device and/or medicine, changed arrangement, contents and/or structure, and/or any other suitable discrepancy, and locally adjust the configuration information according to the local discrepancies.

As indicated in block 230, for example, based on the adjusted configuration information, processor 22 adapts local configuration database 45 according to a current state of smart container 10, such as equipment included in container 10, structure and/or arrangement of container 10, and/or location of container 10.

For example, processor 22 adapts local configuration database 45 to include in the displayable pages references to particular equipment, devices and/or kinds of devices stored and/or storable in container 10, and to exclude from the displayable pages references to particular equipment, devices and/or kinds of devices not storable in container 10. For example, based on the adjusted configuration information, processor 22 adapts database 45 to include in the displayable pages references to sensors, medications and/or supplies included in container 10, and to exclude references to sensors, medications and/or supplies not included in container 10. For example, based on the configuration information, processor 22 adapts database 45 to include in the displayable pages references to a particular structure and/or arrangement included in container 10, for example particular structure and/or arrangement of storage compartments 12. For example, based on the configuration information, processor 22 adapts database 45 to include in the displayable pages information relevant to where the particular container 10 is placed, for example in a school, a clinic, a nursing home and/or any other suitable location. For example, based on the configuration information, processor 22 adapts database 45 to include in the displayable pages instructions to use particular features facilitated by container 10 and/or device 20, such as phone and/or video calls. For example, based on the adjusted configuration information, processor 22 adapts database 45 to exclude from the displayable pages references unsuitable to the structure, arrangement, location and/or available features of container 10.

As indicated in block 240, once a state of container 10 changes, processor 22 may adapt database 45 according to the change. For example, local database 45 may be updated when changes occur in equipment included in container 10, structure and/or arrangement of container 10, and/or location of container 10. For example, processor 22 may adapt database 45 in case a medication is consumed, in case an inventory of medications is renewed, in case container 10 can't connect to a network, in case some feature is broken, fixed or added to container 10, and or any other suitable change.

For example, processor 22 adapts database 45 to disable and/or remove from a displayable page a link or button for calling an emergency or any other number, in case network connectivity is down. For example, processor 22 adapts database 45 to disable and/or remove from a displayable page a link or button to present a location of a device in container 10, in case the device is not available in the particular smart container. For example, processor 22 adapts database 45 to add to displayable page with information about a location of certain equipment within the particular smart container 10.

Based on the local configuration information stored in local configuration database 45, computing device 20 may perform enhancement of the displayable database pages. For example, computing device 20 adds to a page corresponding links, buttons, notes, alerts and/or instructions, and/or automatically performs required operations based on displayed instructions.

Figure 3:
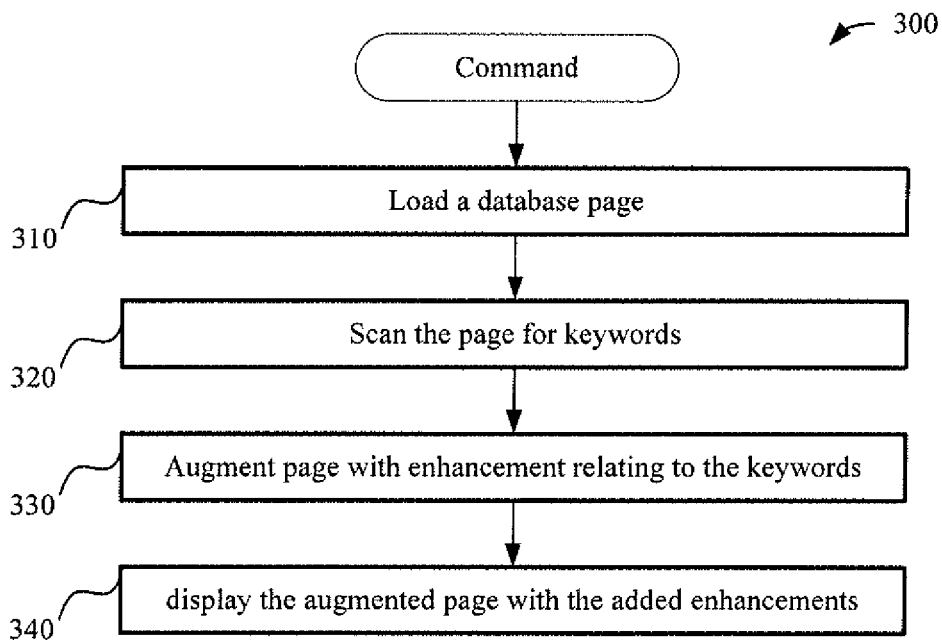
FIG. 3 is a schematic flowchart illustrating a method for locally enhancing an interactive database page, according to some embodiments of the present invention.

Reference is now made to FIG. 3, which is a schematic flowchart illustrating a method 300 for locally enhancing an interactive database page, according to some embodiments of the present invention. As indicated in block 310, processor 22 may load a displayable page of database 40, for example in response to a command received via the user interface. For example, computing device 20 may download the page of database 40, for example a web page, via server 30.

As indicated in block 320, processor 22 may scan the displayable page for keywords and/or combinations of keywords included in local configuration database 45.

In case a keyword is found, as indicated in block 330, processor 22 may augment the page with a corresponding action, link, button, note, alert and/or any other suitable enhancement, as described herein. For example, when source code of a database page is downloaded, for example HyperText Markup Language (HTML) code of the page, processor 22 may scan the code for keywords included in local configuration database 45. Once a keyword is located, processor 22 may modify the code to include a corresponding action, link, widget, button, note, alert and/or any other suitable enhancement. When scanning for keywords, processor 22 may use add on words to generate the enhancement. For example, if a page includes a text saying "Call 866-231-9876" or "Call Poison Control", processor 22 may identify the word "call" as a keyword, and may use the number or term following the word "call" inside the enhancement as the number that should be called, for example in a hyperlink or widget, for example created in JavaScript or any other suitable language. For example, if a page includes a text reciting an instruction such as, for example, "check heartrate", processor 22 may identify one or more of the words of the instruction, for example "check" and/or "heartrate", as keywords, and may enhance the page by a hyperlink, bottom, pop-up, widget and/or any other suitable enhancement, for example for initiating operation of a heartrate testing device and/or a guide for heartrate measurement.

In some embodiments of the present invention, processor 22 changes properties of elements of the page based on information included in local configuration database 45. For so example, a link in the page, original or enhanced, may have different appearance based on information included in local configuration database 45. For example, in case smart container 10 lacks or is out of a certain equipment type or unit, the link may be deactivated or represented by different color, font, size and/or another suitable property, than in case container 10 contains the equipment type or unit.

As indicated in block 340, processor 22 may display the augmented database page with the added enhancements. For example, text content like "Call 911" or "Tylenol" may a become active links and/or widgets.

In some embodiments of the present invention, local configuration database 45 may include indication that certain equipment that is usually included in container 10 is currently missing and/or dysfunctional. In such cases, for example, processor 22 may generate and/or display a corresponding alert, for example a textual alert about the equipment being missing or dysfunctional.

Figure 4:
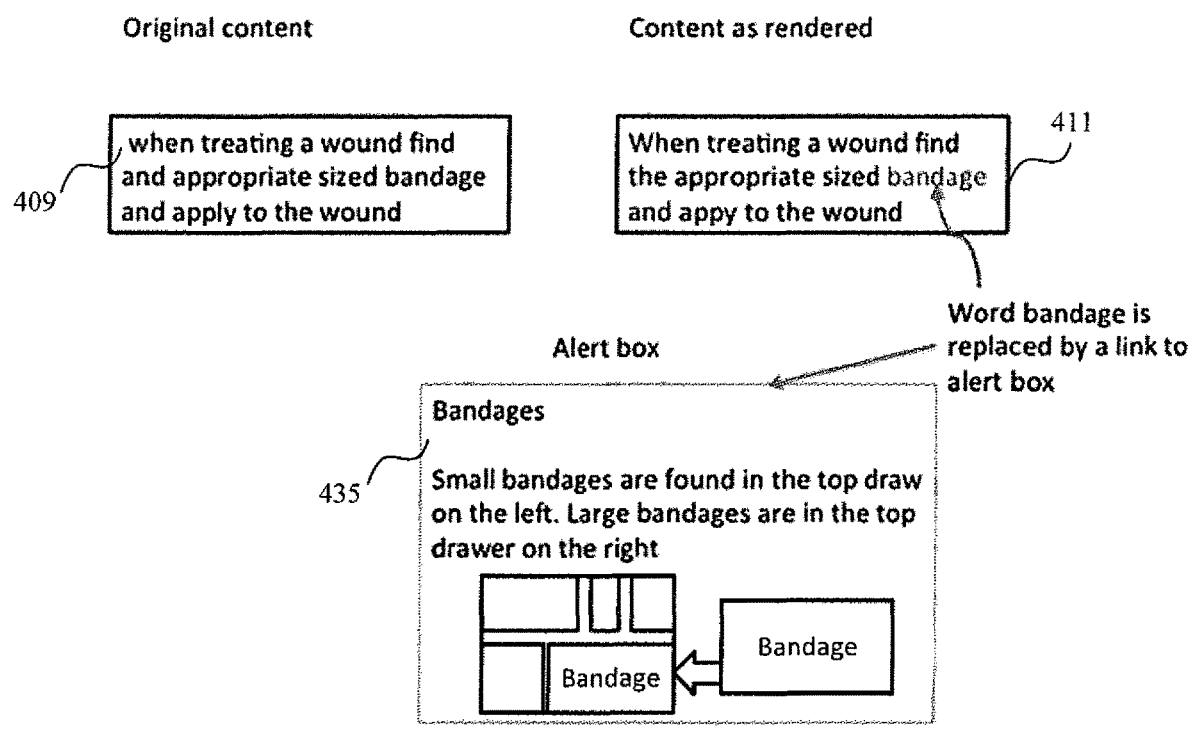
FIG. 4 is a schematic illustration of database page enhancement according to some embodiments of the present invention.

Reference is now made to FIG. 4, which is a schematic illustration of database page enhancement according to some embodiments of the present invention. For example, a database page may include a text box 409. Text box 409 may include text reciting "when treating a wound find an appropriate sized bandage and apply to the wound". For example, local configuration database 45 includes an indication that smart container 10 contains a bandages of various sizes in respective locations, for example small bandages in a top drawer on the left and large bandages in the top drawer on the right. Processor 22 may identify the keyword "Bandage" as a combination included in local configuration database 45, for example as equipment stored in smart container 10. Accordingly, processor 22 may add to the database page an alert box 435 and/or a hyperlink to cause alert box 435 to appear when activated, for example by converting the keyword "bandage" to the hyperlink, as shown in revised text box 411. Alert box 435 may include, for example, a text explaining respective locations of bandages of various sizes and/or an image of the drawer arrangement of contents, the location of a desired object within the drawer and/or an image of the desired object, for example a bandage box.

Figure 5:
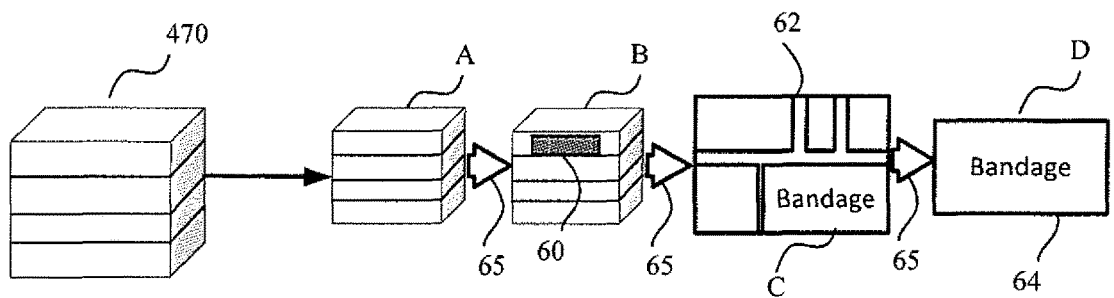
FIG. 5 is a schematic illustration of an interactive and/or dynamic graphic element, for example a widget, according to some embodiments of the present invention.

Reference is now made to FIG. 5, which is a schematic illustration of an interactive and/or dynamic graphic element 470, for example a widget, which may be added by processor 22 as enhancement to a database page, according to some embodiments of the present invention. Graphic element 470 may include a series of images A, B C and D, so appearing in a predefined order. For example, one image may appear at the same location of the previous image after the previous image fades, or all the images may appear one next to the other, for example with arrows 65 showing the order of images.

Dynamic graphic element 470 may show where an equipment unit of interest is located in smart container 10. For example, the equipment unit of interest may be the bandage "Tefla nonstick bandage" or any other piece of equipment referred to by a displayed database page. For example, image A illustrates smart container 10. For example, image B illustrates smart container 10 with a marking 60 showing in which compartment of container 10 the equipment unit is stored. For example, image C illustrates the arrangement of contents within the respective container, for example where a user may identify the equipment unit of interest. In some embodiments, image C includes an indication 62 of the location of the desired equipment unit. For example, image D includes an image 64 of the equipment unit of interest, for example so that a user may see how the unit looks like and identify the unit within the respective compartment.

Figure 6:
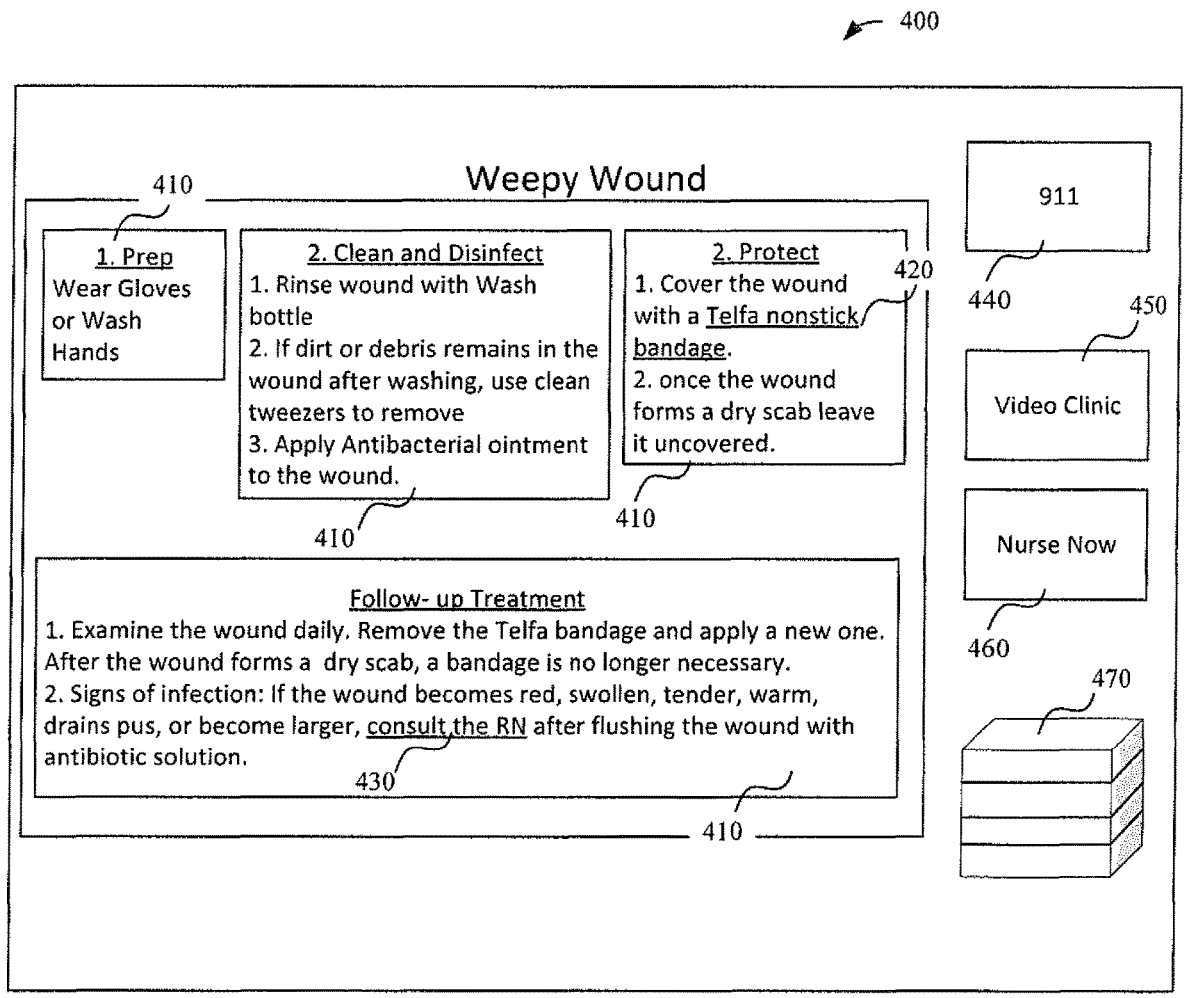
FIG. 6 is a schematic illustration of an enhanced database page, according to some embodiments of the present invention.

Reference is now made to FIG. 6, which is a schematic illustration of an enhanced database page 400, according to some embodiments of the present invention. Page 400 may include one or more text boxes 410 including a set of treatment instructions, for example instructions how to treat a weepy wound. For example, a text box 410 includes a text reciting an instruction to use "Tefla nonstick bandage". For example, local configuration database 45 includes an indication that smart container 10 contains a Tefla nonstick bandage at a third dedicated location in a first compartment. Processor 22 may identify the keyword combination "Tefla nonstick bandage" as a combination included in local configuration database 45, for example as equipment stored in smart container 10. Accordingly, computing device 20 may add to database page 400 a textual note, a hyperlink 420 and/or a graphic element 470 showing and/or informing where the bandage "Tefla nonstick bandage" is located in smart container 10, when and/or how to use it. In some embodiments, processor 22 may add relevant information box in an existing window, in a separate tab and/or a popup window, for example linked to by the hyperlink.

For example, database page 400 includes in a text box 410 an instruction to consult with a registered nurse (RN). For example, database page 400 includes a text reciting "consult the RN", or "if the patent temperature is above 40 degrees, call the nurse". Local configuration database 45 may include an indication that smart container 10 and/or device 20 has calling capabilities for calling a nurse, and/or chat capabilities for chatting with a nurse. According to the identified keyword(s), and/or according to the indication in configuration database 45, computing device 20 may add to database page 400 a hyperlink 430 and/or an interactive graphic element 460 such as a call or a chat button, enabling a call or a chat by communication interface 16 and/or 26. Computing device 20 may add the hyperlink, for example, by converting the identified keyword(s) to a hyperlink, which activates calling to a specific number or initiating a chat.

For example, database page 400 includes a text of automated or real nurse response, for example during a chat. Local configuration database 45 may include an indication that smart container 10 and/or device 20 has video clinic session capabilities. Computing device 20 may scan the nurse response and according to its contents, and/or based on the indication in configuration database 45, if necessary, initiate a video visit to a clinic, and/or display a video button 450 for initiation of a video visit to a clinic.

For example, database page 400 includes in a text box 410 an instruction to call an emergency number, for example "call 911". For example, local configuration database 45 includes an indication that smart container 10 and/or device 20 has calling capabilities for calling the emergency number. Computing device 20 may identify the keywords in the text box, for example "call 911". Based on the identification of the keywords and/or based on the indication in configuration database 45, computing device 20 may add to database page 400 a hyperlink and/or a graphic element 440 such as an emergency call button, enabling a call to the emergency number by communication interface 16 and/or 26.

In the context of some embodiments of the present disclosure, by way of example and without limiting, terms such as 'operating' or 'executing' imply also capabilities, such as 'operable' or 'executable', respectively.

Conjugated terms such as, byway of example, 'a thing property' implies a property of the thing, unless otherwise clearly evident from the context thereof.

The terms 'processor' or 'computer', or system thereof are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically so claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A smart storage container apparatus for storing items of medical equipment, the apparatus comprising:
    at least one storage compartment for storing a plurality of items of medical equipment at a respective plurality of distinct predefined locations in the at least one storage compartment;
    a plurality of detectors in the at least one storage compartment for detecting a presence of each of the plurality of items of medical equipment at the plurality of predefined locations corresponding to each of the plurality of items of medical equipment in the at least one storage compartment, each predefined location having a detector to detect a presence of a corresponding item of medical equipment at the predefined location, the detector being of a type from the group consisting of: a micro-switch, a physical switch, a magnetic detector, a Hall Effect detector, and a radio frequency identification (RFID) detector,
    a communication interface for communicating with a server;
    a display for displaying an interactive user interface; and
    a processor configured to execute code instructions for:
        downloading from the server a local configuration database and one or a plurality of webpages with medical information for display on the interactive user interface;
        identifying using the detected presence at the plurality of predefined locations by the plurality of detectors, items from the one or more items of medical equipment not stored in the at least one storage compartment at the predefined locations;
        searching the one or said plurality of webpages for at least one keyword included in the local configuration database;
        augmenting the one or said plurality of webpages with an enhancement by converting the at least one keyword into a hyperlink or a pop-up that identifies a location of an item of medical equipment stored in the at least one storage compartment, the item of medical equipment corresponding to the at least one keyword;
        displaying an augmented webpage from the one or said plurality of augmented webpages;
        deactivating the enhancement of the displayed augmented webpage by terminating a previously activated webpage component if the at least one keyword is related to identified items of medical equipment not stored in the at least one storage compartment at the predefined locations; and
        in response to a command by a user via the interactive user interface to receive information about an item from the one or more items of medical equipment stored in the at least one storage compartment at the predefined locations, displaying information about the item including a location of the item at the predefined location in the at least one storage compartment.

2. The apparatus of claim 1, wherein the processor is configured to execute code instructions for adjusting the downloaded local configuration database according to particular features or to a particular environment of the apparatus.

3. The apparatus of claim 1, wherein the processor is configured to execute code instructions for adjusting the downloaded local configuration database according to at least one of a list consisting of: particular equipment, devices or kinds of devices stored in the apparatus, a particular structure or arrangement of the at least one storage compartment, and information relevant to where the apparatus is placed.

4. The apparatus of claim 1, wherein the processor is configured to execute code instructions for finding local discrepancies in the downloaded local configuration database from local conditions of die at least one storage compartment and adjusting the downloaded local configuration database according to the local discrepancies.

5. The apparatus of claim 4, wherein the local discrepancies are selected from a group consisting of a missing equipment, a missing device, a missing medicine, a changed arrangement, a changed contents and a changed structure.

6. The apparatus of claim 1, wherein the processor is configured to execute code instructions for adapting the local configuration database according to a current state of the apparatus.

7. The apparatus of claim 1, wherein the processor is configured to execute code instructions for augmenting the one or said plurality of webpages by adding or changing an interactive graphic element for initiating an action, the action corresponding to an indication in the local configuration database that the action is feasible by the apparatus.

8. The apparatus of claim 1, wherein the processor is configured to execute code instructions for augmenting die one or said plurality of webpages by initiating or changing an action in response to the at least one keyword, the action corresponding to an indication in the local configuration database that die action is feasible by the apparatus.

9. The apparatus of claim 1, wherein the enhancements are selected from the group consisting of a hyperlink, a pop-up, a widget, a telephone number to be called, an action, a button, a note and an alert.

10. The apparatus of claim 1, wherein the enhancement comprises a hyperlink, and wherein the processor is configured to execute code instructions for deactivating the enhancement by deactivating the hyperlink to webpages with information about the identified items of medical equipment not stored in the at least one storage compartment at the predefined locations.

11. A smart storage method for storing items of medical equipment, the method comprising:

in a smart storage apparatus comprising a processor, at least one storage compartment for storing a plurality of items of medical equipment at a respective plurality of distinct predefined locations in the at least one storage compartment, a plurality of detectors in the at least one storage compartment for detecting a presence of each of the plurality of items of medical equipment at the plurality of predefined locations corresponding to each of the plurality of items of medical equipment in the at least one storage compartment, each predefined location having a detector to detect a presence of a corresponding item of medical equipment at the predefined location, the detector being of a type from the group consisting of: a micro-switch, a physical switch, a magnetic detector, a Hall Effect detector, and a radio frequency identification (RFID) detector, a communication interface for communicating with a server, and a display for displaying an interactive user interface:

downloading by the processor from the server, a local configuration database and one or a plurality of webpages with medical information for display on the interactive user interface;

identifying by the processor using the detected presence at the plurality of predefined locations by the plurality of detectors, items from the one or more items of medical equipment not stored in the at least one storage compartment at the predefined locations;

searching by the processor the one or said plurality of webpages for at least one keyword included in the local configuration database;

augmenting by the processor the one or said plurality of webpages with an enhancement by converting the at least one keyword into a hyperlink or a pop-up that identifies a location of an item of medical equipment stored in the at least one storage compartment, the item of medical equipment corresponding to the at least one keyword;

displaying by the processor an augmented webpage from the one or said plurality of augmented webpages;

deactivating by the processor the enhancement of the displayed augmented webpage by terminating a previously activated webpage component if the at least one keyword is related to identified items of medical equipment not stored in the at least one storage compartment at the predefined locations; and in response to a command by a user via the interactive user interface to receive information about an item from the one or more items of medical equipment stored in the at least one storage compartment at the predefined locations, displaying by the processor information about the item including a location of the item at the predefined location in the at least one storage compartment.

12. The method of claim 11, further comprising the downloaded local configuration database according to particular features or to a particular environment of the apparatus.

13. The method of claim 11, further comprising adjusting the downloaded local configuration database according to at least one of a list consisting of: particular equipment, devices or kinds of devices stored in the apparatus, a particular structure or arrangement of the at least one storage compartment, and information relevant to where the apparatus is placed.

14. The method of claim 11, further comprising finding local discrepancies in the downloaded local configuration database from local conditions of the at least one storage compartment and adjusting the downloaded local configuration database according to the local discrepancies.

15. The method of claim 14, wherein the local discrepancies are selected from a group consisting of a missing equipment, a missing device, a missing medicine, a changed arrangement, a changed contents and a changed structure.

16. The method of claim 11, comprising adapting the local configuration database according to a current state of the apparatus.

17. The method of claim 11, wherein augmenting the one or said plurality of webpages comprises adding or changing an interactive graphic element for initiating an action, the action corresponding to an indication in the local configuration database that the action is feasible by the apparatus.

18. The method of claim 11, wherein augmenting the one or said plurality of webpages comprises initiating or changing an action in response to the at least one keyword, the action corresponding to an indication in the local configuration database that the action is feasible by the apparatus.

19. The method of claim 11, wherein the enhancements are selected from the group consisting of a hyperlink, a pop-up, a widget, a telephone number to be called, an action, a button, a note and an alert.

20. The method of claim 11, wherein the enhancement comprises a hyperlink, and wherein deactivating the enhancement comprises deactivating the hyperlink to webpages with information about the identified items of medical equipment not stored in the at least one storage compartment at the predefined locations.

* * * * *